(12) United States Patent
Engels

(10) Patent No.: US 9,474,221 B2
(45) Date of Patent: Oct. 25, 2016

(54) TOMATO VARIETY NUN 09015 TOF

(71) Applicant: Nunhems B.V., AC Nunhem (NL)

(72) Inventor: Coert Engels, AC Nunhem (NL)

(73) Assignee: Nunhems B.V., AC Nunhem (NL)

( * ) Notice: Subject to any disclaimer, the term of this patent is extended or adjusted under 35 U.S.C. 154(b) by 0 days.

(21) Appl. No.: 14/541,397

(22) Filed: Nov. 14, 2014

(65) Prior Publication Data
US 2015/0074839 A1 Mar. 12, 2015

(51) Int. Cl.
*A01H 5/08* (2006.01)
*A01H 1/00* (2006.01)
*C12N 15/00* (2006.01)

(52) U.S. Cl.
CPC .................................... *A01H 5/08* (2013.01)

(58) Field of Classification Search
None
See application file for complete search history.

(56) References Cited

U.S. PATENT DOCUMENTS 8,101,836 B2 * 1/2012 Bile .................... A01H 5/08
435/411

* cited by examiner

*Primary Examiner* — Phuong Bui

(57) ABSTRACT

The invention provides a new and distinct hybrid variety of tomato, NUN 09015 TOF.

15 Claims, No Drawings

TOMATO VARIETY NUN 09015 TOF

FIELD OF THE INVENTION

The present invention relates to the field of plant breeding and, more specifically, to the development of tomato variety NUN 09015 TOF (also designated as NUN 09015 or NUN 09015 TOF).

BACKGROUND OF THE INVENTION

The goal of vegetable breeding is to combine various desirable traits in a single variety/hybrid. Such desirable traits may include greater yield, resistance to diseases, insects or other pests, tolerance to heat and drought, better agronomic quality, higher nutritional value, enhanced growth rate and improved fruit properties.

Breeding techniques take advantage of a plant's method of pollination. There are two general methods of pollination: a plant self-pollinates if pollen from one flower is transferred to the same or another flower of the same genotype. A plant cross-pollinates if pollen comes to it from a flower of a different genotype.

Plants that have been self-pollinated and selected for a uniform type over many generations become homozygous at almost all gene loci and produce a uniform population of true breeding progeny of homozygous plants. A cross between two such homozygous plants of different varieties produces a uniform population of hybrid plants that are heterozygous for many gene loci. The extent of heterozygosity in the hybrid is a function of the genetic distance between the parents. Conversely, a cross of two plants each heterozygous at a number of loci produces a segregating population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new lines are evaluated to determine which of those have commercial potential. One crop species which has been subject to such breeding programs and is of particular value is the tomato.

Tomato (*Solanum lycopersicum* and closely related species) is naturally a diploid and the basic chromosome number of the genus is x=12, most are 2n=2x=24, including the cultivated ones. It originated in the New World and has since become a mayor food crop. In 2012, FAOSTAT estimated world production at over 160 million tonnes.

Tomato cultivars may be grouped by maturity, i.e. the time required from planting the seed to the stage where fruit harvest can occur. Standard maturity classifications include 'early', 'midseason' or late-maturing'. Another classification for tomatoes is the developmental timing of fruit set. 'Determinant' plants grow foliage, then transition into a reproductive phase of flower setting, pollination and fruit development. Consequently, determinant cultivars have a large proportion of the fruit ripen within a short time frame. Growers that harvest only once in a season favor determinant type cultivars. In contrast, 'indeterminate' types grow foliage, then enter a long phase where flower and fruit development proceed along with new foliar growth. Growers that harvest the same plants multiple times favor indeterminate type cultivars. In response to more recent consumer demands for dietary diversity, tomato breeders have developed a wider range of colors. In addition to expanding the range of red colored fruits, there are cultivars that produce fruits that are creamy white, lime green, yellow, green, golden, orange and purple. Additionally, there are multi-colored varieties exemplified by mainly red fruited varieties with green shoulders, and both striped- and variegated-colored fruit.

The fruits of tomato plants which are more suitable for processing are generally red colored and have pink to red/crimson fruit flesh.

SUMMARY OF THE INVENTION

The invention concerns seed of tomato variety NUN 09015 TOF, wherein a representative sample of said seed has been deposited under Accession Number NCIMB 42622. The tomato seed of the invention may be provided as an essentially homogeneous population of tomato seed. Therefore, seed of the invention may be defined as forming at least about 97% of the total seed, including at least about 98%, 99% or more of the seed. The population of tomato seed may be particularly defined as being essentially free from other seed. The seed population may be separately grown to provide an essentially homogeneous population of tomato plants according to the invention. Also encompassed are plants grown from seeds of tomato variety NUN 09015 TOF and plant parts thereof.

In another aspect the invention provides for a hybrid variety of *S. lycopersicum* called NUN 09015 TOF. The invention also provides for a plurality of seeds of the new variety, plants produced from growing the seeds of the new variety NUN 09015 TOF, and progeny of any of these. Especially, progeny retaining one or more (or all) of the "distinguishing characteristics" or one or more (or all) of the "essential morphological and physiological characteristics" or essentially all physiological and morphological characteristics of NUN 09015 TOF referred to herein, are encompassed herein as well as methods for producing these.

In one aspect, such progeny have all the physiological and morphological characteristics of tomato variety NUN 09015 TOF when grown under the same environmental conditions. In another aspect such progeny have all the physiological and morphological characteristics as listed in Table 1 as tomato variety NUN 09015 TOF when measured under the same environmental conditions (i.e. evaluated at significance levels of 1%, 5% or 10% significance, which can also be expressed as a p value).

In another aspect a plant of the invention or said progeny plants has/have 1, 2, 3, 4 or more or all of the distinguishing characteristics: 1) average length of mature fruit (stem axis) of 58.9 to 65.1 mm; 2 average diameter of mature fruit (at widest point) of 44.6 to 49.4 mm; 3) average weight of mature fruit of 67.7 to 74.9 gram; 4) average number of locules of 1.96 to 2.17; 5) an average number of flowers in inflorescence of 7.3 to 8.1; 6) average number of nodes between early inflorescence of 6.2 to 6.9 7) typical fruit shape of type 7; 8) an average length of dedicel (from joint to calyx attachment) of 14.8 to 16.4 mm; 9) pubescence on younger stems of type 3—moderately hairy and 10) a type 3—nippled shape of blossom end, in addition to 3, 4, 5, 6, 7, 8, or more, or all of the other (average) characteristics as listed in Table 1.

Further, a tomato fruit produced on a plant grown from these seeds is provided.

In yet another embodiment of the invention, a plant having one, two or three physiological and/or morphological characteristics which are different from those of NUN 09015 TOF and which otherwise has all the physiological and morphological characteristics of NUN 09015 TOF as listed in Table 1, wherein a representative sample of seed of variety NUN 09015 TOF has been deposited under Accession Number NCIMB 42622, is provided.

Further, a vegetatively propagated plant of variety NUN 70038 PPH, or a part thereof, is provided having all the morphological and physiological characteristics of NUN 09015 TOF when grown under the same environmental conditions.

Also a plant part derived from variety NUN 70038 is provided, wherein said plant part is selected from the group consisting of: fruit, harvested fruit, parts of fruits, leaf, pollen, ovule, cell, part of a leaf, petioles, shoots or parts thereof, stems or parts thereof, roots or parts thereof, cuttings, seeds, hypocotyl, cotyledon, flowers or parts thereof, scion, scion, stock, rootstock and flower. Fruits are particularly important plant parts.

DEFINITIONS

"Tomato" refers herein to plants of the species *Solanum lycopersicum*, or a closely related species, and fruits thereof. *Solanum lycopersicum*, is also known as *Lycopersicon lycopersicum* (L.) *H. Karst.* or *Lycopersicon esculentum* Mill.

"Cultivated tomato" refers to plants of *Solanum lycopersicum*, or a closely related species, i.e. varieties, breeding lines or cultivars of the species *S. lycopersicum* as well as crossbreds thereof, or crossbreds with other *Solanum* species, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of *Solanum* and related species.

The terms "tomato plant designated NUN 09015 TOF", "NUN 09015", "09015 TOF" or "variety designated 09015 TOF" are used interchangeably herein and refer to a tomato plant of variety NUN 09015 TOF, representative seed of which having been deposited under Accession Number NCIMB 42622.

"Tissue culture" refers to a composition comprising isolated cells of the same or a different type or a collection of such cells organized into parts of a plant. Tissue culture of various tissues of tomato and regeneration of plants therefrom is well known and widely published (see, e.g., Bhatia et al. (2004), Plant Cell, Tissue and Organ Culture 78: 1-21. Similarly, the skilled person is well-aware how to prepare a "cell culture".

"UPOV descriptors" are the plant variety descriptors described for tomato in the "Guidelines for the Conduct of Tests for Distinctness, Uniformity and Stability, TG/44/10 (Geneva 2001), as published by UPOV (International Union for the Protection of New Varieties and Plants, available on the world wide web at upov.int) and which can be downloaded from the world wide web at upov.int/en/publications/tg-rom/tg044/tg_44_10.pdf.

"USDA descriptors" are the plant variety descriptors for tomato (*Solanum lycopersicum* or *Lycopersicon esculentum* Mill.) as published by the US Department of Agriculture, Agricultural Marketing Service, Plant Variety Protection Office, Beltsville, Md. 20705 (available on the world wide web at ams.usda.gov) and which can be downloaded from the world wide web at ams.usda.gov/AMSv1.0/getfile?dDocName=STELDEV3003738.

"RHS" refers to the Royal Horticultural Society of England which publishes an official botanical color chart quantitatively identifying colors according to a defined numbering system. The chart may be purchased from Royal Horticulture Society Enterprise Ltd RHS Garden; Wisley, Woking; Surrey GU236QB, UK, e.g., the RHS colour chart: 2007 (The Royal Horticultural Society, charity No: 222879, PO Box 313 London SW1P2PE; sold by, e.g., TORSO-VERLAG, Obere Grüben 8 • D-97877 Wertheim, Article-No.: Art62-00008 EAN-Nr.: 4250193402112).

As used herein, the term "plant" includes the whole plant or any parts or derivatives thereof, preferably having the same genetic makeup as the plant from which it is obtained, such as plant organs (e.g. harvested or non-harvested fruits), plant cells, plant protoplasts, plant cell tissue cultures or tissue cultures from which whole plants can be regenerated, plant calli, plant cell clumps, plant transplants, seedlings, hypocotyl, cotyledon, plant cells that are intact in plants, plant clones or micropropagations, or parts of plants (e.g. harvested tissues or organs), such as plant cuttings, vegetative propagations, embryos, pollen, ovules, fruits, flowers, leaves, seeds, clonally propagated plants, roots, stems, root tips, grafts, scions, rootstocks, parts of any of these and the like. Also any developmental stage is included, such as seedlings, cuttings prior or after rooting, mature plants or leaves.

"Harvested plant material" refers herein to plant parts (e.g. fruits detached from the whole plant) which have been collected for further storage and/or further use.

"Harvested seeds" refers to seeds harvested from a line or variety, e.g. produced after self-fertilization or cross-fertilization and collected.

"Internode" refers to a portion of a plant stem between nodes.

"Node" refers to the place on a plant stem where a leaf is attached.

"Rootstock" or "stock" refers to the plant selected for its roots, in particular for the resistance of the roots to diseases or stress (e.g. heat, cold, salinity etc). Normally the quality of the fruit of the plant providing the rootstock is less important.

"Scion" refers to a part of the plant that is attached to the rootstock. This plant is selected for its stems, leaves, flowers, or fruits. The scion contains the desired genes to be duplicated in future production by the stock/scion plant and may produce the desired tomato fruit.

"Stock/scion" plant refers to a tomato plant comprising a rootstock from one plant grafted to a scion from another plant.

"Grafting" refers to attaching tissue from one plant to another plant so that the vascular tissues of the two tissues join together. Grafting may be done using methods known in the art like: Tongue Approach/Approach Graft, 2) Hole insertion/Terminal/Top Insertion Graft, 3) One Cotyledon/Slant/Splice/Tube Graft and 4) Cleft/Side Insertion Graft A plant having "all the physiological and morphological characteristics" of a referred-to-plant means a plant having the physiological and morphological characteristics of the referred-to-plant when grown under the same environmental conditions, preferably in the same experiment; the referred-to-plant can be a plant from which it was derived, e.g. the progenitor plant, the parent, the recurrent parent, the plant used for tissue- or cell culture, etc.

A plant having "essentially all the physiological and morphological characteristics" of a referred-to-plant means a plant having all the (e.g. 1-10) distinguishing physiological and morphological characteristics (distinguishing characteristics as herein defined) when grown under the same environmental conditions of the referred-to-plant (e.g. a plant from which it was derived such as the progenitor plant, the parent, the recurrent parent, the plant used for tissue- or cell culture, etc.) Alternatively, a plant having "essentially all the physiological and morphological characteristics" of a referred-to-plant means a plant having all the characteristics as listed in Table 1 when grown under the same environmental conditions as a referred-to-plant (e.g. a plant from which it was derived such as the progenitor plant, the parent, the recurrent parent, the plant used for tissue- or cell culture, etc.). In another embodiment, a plant having "essentially all the physiological and morphological characteristics" of a referred-to-plant means a plant having all but 1, 2, 3, 4 or 5 of the characteristics as listed in Table 1 when grown under the same environmental conditions as a referred-to-plant (e.g. a plant from which it was derived such as the progenitor plant, the parent, the recurrent parent, the plant used for tissue- or cell culture, etc.).

For NUN 09015 TOF the distinguishing characteristics are 1) average length of mature fruit (along stem axis); 2 average diameter of mature fruit (at widest point); 3) average weight of mature fruit; 4) average number of locules; 5) an average number of flowers in inflorescence; 6) average number of nodes between early inflorescence; 7) typical fruit shape of type 7; 8) an average length of dedicel (from joint to calyx attachment); 9) pubescence on younger stems and 10) shape of blossom end.

In certain embodiments the plant of the invention has all the physiological and morphological characteristics, except for certain characteristics mentioned, e.g. the characteristic(s) derived from a converted or introduced gene or trait and/or except for the characteristics which differ.

Similarity between different plants is defined as the number of distinguishing characteristics (or the characteristics as listed in Table 1) that are the same between the two plants that are compared when grown under the same environmental conditions. Characteristics are considered "the same" when the value for a numeric characteristic is evaluated at significance levels of 1%, 5% or 10% significance level, or when a non-numeric characteristic is identical, if the plants are grown under the same conditions.

A plant having one or more "essential physiological and/or morphological characteristics" or one or more "distinguishing characteristics" refers to a plant having (or retaining) one or more of the characteristics mentioned in Table 1 when grown under the same environmental conditions that distinguish NUN 09015 TOF from the most similar varieties (such as variety Daniela), such as but not limited to average number of fruits per plant, heat of (dried) fruit, maturity, average fruit diameter at mid-point or average fruit length.

"Distinguishing characteristics" or "distinguishing morphological and/or physiological characteristics" refers herein the characteristics which are distinguishing between NUN 09015 TOF and other tomato varieties, such as Daniela, when grown under the same environmental conditions, especially the following characteristics: 1) an average length of mature fruit (stem axis) of 58.9 to 65.1 mm; 2 average diameter of mature fruit (at widest point) of 44.6 to 49.4 mm; 3) average weight of mature fruit of 67.7 to 74.9 gram; 4) average number of locules of 1.96 to 2.17; 5) an average number of flowers in inflorescence of 7.3 to 8.1; 6) average number of nodes between early inflorescence of 6.2 to 6.9 7) typical fruit shape of type 7; 8) an average length of dedicel (from joint to calyx attachment) of 14.8 to 16.4 mm; 9) pubescence on younger stems of type 3—moderately hairy and 10) a type 3—nippled shape of blossom end. In one aspect, the distinguishing characteristics further include at least one, two, three or more (or all) of the characteristics listed in Table 1. All numerical distinguishing characteristics are statistically significantly different at $p<0.05$.

Thus, a tomato plant "comprising the distinguishing characteristics of "NUN 09015 TOF" refers herein to a tomato plant which does not differ significantly from NUN 09015 TOF in characteristics 1) to 5) above. In a further aspect the tomato plant further does not differ significantly from NUN 09015 TOF in one or more, or all characteristics 6) to 10) as mentioned above. In yet a further aspect the tomato plant further does not differ in at least one, two, three, four, five or six (or all) characteristics selected from the characteristics listed in Table 1. In still another aspect the tomato plant does not differ in any of the distinguishing characteristics 1) to 10) listed above.

The physiological and/or morphological characteristics mentioned above are commonly evaluated at significance levels of 1%, 5% or 10%, when measured under the same environmental conditions. For example, a progeny plant of NUN 09015 TOF may have one or more (or all) of the essential physiological and/or morphological characteristics of NUN 09015 TOF listed in Table 1, as determined at the 5% significance level when grown under the same environmental conditions.

As used herein, the term "variety", "cultivated tomato" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

A variety is referred to as an "Essentially Derived Variety" (EDV) i.e., shall be deemed to be essentially derived from another variety, "the initial variety" when (i) it is predominantly derived from the initial variety, or from a variety that is itself predominantly derived from the initial variety, while retaining the expression of the essential characteristics that result from the genotype or combination of genotypes of the initial variety; (ii) it is clearly distinguishable from the initial variety; and (iii) except for the differences which result from the act of derivation, it conforms to the initial variety in the expression of the essential characteristics that result from the genotype or combination of genotypes of the initial variety. Thus, an EDV may be obtained for example by the selection of a natural or induced mutant, or of a somaclonal variant, the selection of a variant individual from plants of the initial variety, backcrossing, or transformation by genetic engineering.

"Plant line" is for example a breeding line which can be used to develop one or more varieties. Progeny obtained by selfing a plant line has the same phenotype as its parents.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Regeneration" refers to the development of a plant from cell culture or tissue culture or vegetative propagation.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting of) leaf, pollen, embryo, cotyledon, hypocotyl, cells, protoplasts, meristematic cell, root, root tip, pistil, anther, flower, shoot tip, shoot, stem, fruit, petiole, etc. When a whole plant is regenerated by vegetative propagation, it is also referred to as a vegetative propagation.

"Selfing" refers to self-pollination of a plant, i.e., the transfer of pollen from the anther to the stigma of the same plant.

"Crossing" refers to the mating of two parent plants. The term encompasses "cross-pollination" and "selfing".

"Cross-pollination" refers to the fertilization by the union of two gametes from different plants.

"Substantially equivalent" refers to a characteristic that, when compared, does not show a statistically significant difference (e.g., p=0.05) from the mean. ANOVA is a suitable method for determining the value of p (Clewer, A. G., and D. H. Scarisbrick. 2001).

"Locus" (plural loci) refers to the specific location of a gene or DNA sequence on a chromosome. A locus may confer a specific trait.

"Allele" refers to one or more alternative forms of a gene locus. All of these loci relate to one trait. Sometimes, different alleles can result in different observable phenotypic traits, such as different pigmentation. However, many variations at the genetic level result in little or no observable variation. If a multicellular organism has two sets of chromosomes, i.e. diploid, these chromosomes are referred to as homologous chromosomes. Diploid organisms have one copy of each gene (and therefore one allele) on each chromosome. If both alleles are the same, they are homozygotes. If the alleles are different, they are heterozygotes.

"Genotype" refers to the genetic composition of a cell or organism.

"Phenotype" refers to the detectable characteristics of a plant, cell or organism, which characteristics are the manifestation of gene expression.

Haploid" refers to a cell or organism having one set of the two sets of chromosomes in a diploid.

"Diploid" refers to a cell or organism having two sets of chromosomes.

"Polyploid" refers to a cell or organism having three or more complete sets of chromosomes.

"Triploid" refers to a cell or organism having three sets of chromosomes.

"Tetraploid" refers to a cell or organism having four sets of chromosomes.

"Maturity" refers to the fruit developmental stage when the fruit has fully developed (reached its final size), begins to ripen and undergoes ripening, during which fruits can be divided into 1, 2, 3 or more maturity stages. Thereafter, fruits become overripe. In particular embodiments "maturity" is defined as the mature stage of fruit development and optimal time for harvest. In one embodiment a "mature" tomato is defined as having reached the stage of maturity which will insure the proper completion of the normal ripening process. In particular embodiments, fruit should be harvested at a maturity stage i.e. substantially near maximum sweetness and flavor intensity.

"Harvest maturity" is referred to as the stage at which a tomato fruit is ripe or ready for harvest or the optimal time to harvest the fruit. In one embodiment, harvest maturity is the stage which allows proper completion of the normal ripening.

"Flavor" (or flavour) refers to the sensory impression of a food or other substance, especially a tomato fruit or fruit part (fruit flesh) and is determined mainly by the chemical senses of taste and smell. Flavor is influenced by texture properties and by volatile and/or non-volatile chemical components (organic acids, lipids, carbohydrates, salts etc.).

The term "traditional breeding techniques" encompasses herein crossing, selfing, selection, double haploid production, embryo rescue, protoplast fusion, marker assisted selection, mutation breeding etc. as known to the breeder (i.e. methods other than genetic modification/transformation/transgenic methods), by which, for example, a genetically heritable trait can be transferred from one tomato line or variety to another.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce progeny plants. Progeny plants which have the trait are then crossed to the recurrent parent. After several generations of backcrossing and/or selfing the recurrent parent comprises the trait of the donor. The plant generated in this way may be referred to as a "single trait converted plant".

"Progeny" as used herein refers to plants derived from a plant designated NUN 09015 TOF. Progeny may be derived by regeneration of cell culture or tissue culture or parts of a plant designated NUN 09015 TOF or selfing of a plant designated NUN 09015 TOF or by producing seeds of a plant designated NUN 09015 TOF. In further embodiments, progeny may also encompass plants derived from crossing of at least one plant designated NUN 09015 TOF with another tomato plant of the same or another variety or (breeding) line, or wild tomato plants, backcrossing, inserting of a locus into a plant or mutation. A progeny is, e.g., a first generation progeny, i.e. the progeny is directly derived from, obtained from, obtainable from or derivable from the parent plant by, e.g., traditional breeding methods (selfing and/or crossing) or regeneration. However, the term "progeny" generally encompasses further generations such as second, third, fourth, fifth, sixth, seventh or more generations, i.e., generations of plants which are derived from, obtained from, obtainable from or derivable from the former generation by, e.g., traditional breeding methods, regeneration or genetic transformation techniques. For example, a second generation progeny can be produced from a first generation progeny by any of the methods mentioned above.

The terms "gene converted" or "conversion plant" in this context refer to tomato plants which are developed by backcrossing wherein essentially all of the desired morphological and physiological characteristics of parent are recovered in addition to the one or more genes transferred into the parent via the backcrossing technique or via genetic engineering. Likewise a "Single Locus Converted (Conversion) Plant" refers to plants which are developed by plant breeding techniques comprising or consisting of backcrossing, wherein essentially all of the desired morphological and physiological characteristics of a tomato variety are recovered in addition to the characteristics of the single locus having been transferred into the variety via the backcrossing technique and/or by genetic transformation.

"Transgene" or "chimeric gene" refers to a genetic locus comprising a DNA sequence which has been introduced into the genome of a tomato plant by transformation. A plant comprising a transgene stably integrated into its genome is referred to as "transgenic plant".

"Linkage" refers to a phenomenon wherein alleles on the same chromosome tend to segregate together more often than expected by chance if their transmission was independent.

"Marker" refers to a readily detectable phenotype, preferably inherited in codominant fashion (both alleles at a locus in a diploid heterozygote are readily detectable), with no environmental variance component, i.e., a heritability of 1.

"Average" refers herein to the arithmetic mean.

The term "mean" refers to the arithmetic mean of several measurements. The skilled person understands that the appearance of a plant depends to some extent on the growing conditions of said plant. Thus, the skilled person will know typical growing conditions for tomatoes described herein. The mean, if not indicated otherwise within this application, refers to the arithmetic mean of measurements on at least 10 different, randomly selected plants of a variety or line.

DETAILED DESCRIPTION

The present invention relates to a *Solanum lycopersicum* variety, referred to as NUN 09015 TOF, which has a higher average number of seeds per fruit, greater heat of (dried) fruit, earlier maturity, lower average plant height, lower average plant width, lower average seed cavity diameter, concentrated fruit set instead of scattered fruit set, higher average placental length, lower average fruit flesh thickness and higher average third internode length than check variety Daniela. Also encompassed by the present invention are progeny plants having all but 1, 2, or 3 of the morphological and/physiological characteristics of NUN 09015 TOF and methods of producing plants in accordance with the present invention.

A tomato plant of NUN 09015 TOF differs from the most similar comparison variety Daniela in one or more characteristics (referred herein to as "distinguishing characteristics" or "distinguishing morphological and/or physiological characteristics" (or essential physiological and/or morphological characteristics) selected from:

1) NUN 09015 TOF has an average length of mature fruit (stem axis) that is at least 10%, or preferably 15, 20, 25, 26% or even more preferably about 27% higher than Daniela;
2) NUN 09015 TOF has an average diameter of mature fruit (at widest point) that is at least 10%, or preferably 15, 16, 225, 17, 18% or even more preferably about 18.7% lower than Daniela;
3) NUN 09015 TOF has an average weight of mature fruit that is at least 10%, or preferably 15, 20, 21, 22% or even more preferably about 22.9% lower than Daniela;
4) NUN 09015 TOF has an average number of locules that is at least 20%, or preferably 25, 30, 35, 36% or even more preferably about 37% lower than Daniela;
5) NUN 09015 TOF has an average number of flowers in inflorescence that is at least 15%, or preferably 20, 25, 27.5, 30% or even more preferably about 31% higher than Daniela;
6) NUN 09015 TOF has an average number of nodes between early inflorescence that is at least 10%, or preferably 12, 13, 15, 16% or even more preferably about 16.6% higher than Daniela;
7) NUN 09015 TOF has a typical fruit shape of type 7 instead of a type 2 which Daniela has;
8) NUN 09015 TOF has an average length of dedicel (from joint to calyx attachment) that is at least 10%, or preferably 12 14, 15, 16% or even more preferably about 17% longer than Daniela;
9) NUN 09015 TOF has pubescence on younger stems of type 3—moderately hairy instead of a type 2—sparsely hairy which Daniela has; and
10) NUN 09015 TOF has a type 3—nippled shape of blossom end instead of a type 2—flat which Daniela has.

It is understood that "significant" differences refer to statistically significant differences, when comparing the characteristic between two plant lines or varieties when grown under the same conditions. Preferably at least about 10, 15, 20 or more plants per line or variety are grown under the same conditions (i.e. side by side) and characteristics are measured on at least about 10, 15, 20 or more randomly selected plant or plant parts to obtain averages. Thus, physiological and morphological characteristics or traits are commonly evaluated at a significance level of 1%, 5% or 10%, when measured in plants grown under the same environmental conditions.

Thus, in one aspect, the invention provides seeds of the tomato variety designated NUN 09015 TOF wherein a representative sample of seeds of said variety was deposited under the Budapest Treaty, with Accession number NCIMB 42622.

Seeds of NUN 09015 TOF are obtainable by crossing the male parent with the female parent and harvesting the seeds produced on the female parent. The resultant NUN 09015 TOF seeds can be grown to produce NUN 09015 TOF plants. In one embodiment a plurality of NUN 09015 TOF seeds are packaged into small and/or large containers (e.g., bags, cartons, cans, etc.). The seeds may be disinfected, primed and/or treated with various compounds, such as seed coatings or crop protection compounds.

Also provided are plants of tomato variety NUN 09015 TOF, or a fruit or other plant part thereof, produced from seeds, wherein a representative sample of said seeds has been deposited under the Budapest Treaty, with Accession Number NCIMB 42622. Also included is a cell culture or tissue culture produced from such a plant or a plant regenerated from such a cell or tissue culture said plant expressing all the morphological and physiological characteristics of NUN 09015 TOF.

Plants of NUN 09015 TOF can be produced by seeding directly in the ground (e.g., field) or by germinating the seeds in controlled environment conditions (e.g., greenhouses) and then transplanting the seedlings into the field. For example, the seed can be sown into prepared seed beds where they will remain for the entire production of the crop. Alternatively, the tomato seed may be planted through a black plastic mulch. The dark plastic will absorb heat from the sun, warming the soil early. It will also help to conserve moisture during the growing season, controls weeds and makes harvesting easier and cleaner. Tomato can also be grown entirely in greenhouses. See for example M Domis, A P Papadopoulos (2002) Horticultural Reviews for cultivation, harvesting, handling and postharvest methods commonly used.

In another aspect, the invention provides for a tomato plant of variety NUN 09015 TOF, a representative sample of seed from said variety has been deposited under the Budapest Treaty, with Accession number NCIMB 42622.

In other aspects, the invention provides for a fruit of tomato variety NUN 09015 TOF, or a plant part, such as pollen, flowers, shoots or cuttings of variety NUN 09015 TOF or parts thereof.

In one embodiment any plant of the invention comprises at least 3, 4, 5 or more, e.g. 6, 7, 8, 9 or all of the following morphological and/or physiological characteristics (i.e. distinguishing characteristics (average values; measured at harvest or market maturity, as indicated on the USDA Objective description of variety—Tomato (unless indicated otherwise), when grown under the same environmental conditions):

1) NUN 09015 TOF has an average length of mature fruit (stem axis) of about 62 mm e.g. between about 45 and about 80 or preferably between about 50 and about 75 or between about 55 and 70 or even between about 60 and 65 seeds; 1) of 58.9 to 65.1 mm; 2 of 44.6 to 49.4 mm; 3) of 67.7 to 74.9 gram; 4) average of 1.96 to 2.17; 5) an of 7.3 to 8.1; 6) of 6.2 to 6.9 7; 8) an average of 14.8 to 16.4 mm; 9) pubescence on younger stems of type 3—moderately hairy and 10) a type 3—nippled shape of blossom end.
2) NUN 09015 TOF has an average diameter of mature fruit (at widest point) of about 47 mm e.g. between about 30 mm and about 65 mm or preferably between about 35 and about 60 mm or between about 40 and 55 mm or even between about 45 and 50 mm;
3) NUN 09015 TOF has average weight of mature fruit of about 71.3 gram e.g. between about 65 and about 80 g or preferably between about 68 and about 77 g or between about 70 and 74 g or even between about 71 and 72 g;
4) NUN 09015 TOF has an average number of locules of class 1: approximately two locules;
5) NUN 09015 TOF has an average number of flowers in inflorescence of about 7.7 e.g. between about 6.5 and about 9.0 or preferably between about 7.0 and about 8.5 or between about 7.5 and 8.0 or even between about 7.6 and 7.8.
6) NUN 09015 TOF has an average number of nodes between early inflorescence of about 6.53 e.g. between about 6 and about 8 or preferably between about 6.5 and about 7.5 or between about 6.00 and 7.00 or even between about 6.25 and 6.75;
7) NUN 09015 TOF has a typical fruit shape of type 7;
8) NUN 09015 TOF has an average length of dedicel (from joint to calyx attachment) of about 15.6 mm e.g. between about 10 mm and about 20 mm or preferably between about 12 and about 18 mm or between about 14 and 17 mm or even between about 15 and 16 mm;
9) NUN 09015 TOF has pubescence on younger stems that is type 3—moderately hairy; and
10) NUN 09015 TOF has a type 3—nippled shape of blossom end of the fruit.

In another embodiment, NUN 09015 TOF has intermediate to high resistance against the viral diseases Tomato Mosaic Virus strain 0,1 and 2 and the fungal diseases *Verticillium dahlia* Race 0, *Fusarium oxysporum* f. sp. *Lycopersici* race 0 and 1, *Cladosporium fulvum* race 0 group A, B, C, D, and E, All resistances are classified as high (9 out of 9, with 9 highest. All Rates are from 1 (most susceptible) to 9 (most resistant.

In still another aspect the invention provides a method of producing a tomato plant, comprising crossing a plant of tomato variety NUN 09015 TOF with a second tomato plant one or more times, and selecting progeny from said crossing.

In yet another aspect the invention provides a method of producing a tomato plant, comprising selfing a plant of tomato variety NUN 09015 TOF one or more times, and selecting progeny from said selfing.

In other aspects, the invention provides for progeny of variety NUN 09015 TOF such as progeny obtained by further breeding NUN 09015 TOF. Further breeding NUN 09015 TOF includes selfing NUN 09015 TOF one or more times and/or cross-pollinating NUN 09015 TOF with another tomato plant or variety one or more times. In particular, the invention provides for progeny that retain all the essential morphological and physiological characteristics of NUN 09015 TOF or that retain one or more of the distinguishing characteristics of the tomato type described further above and when grown under the same environmental conditions. In another aspect, the invention provides for vegetative reproductions of the variety and plants having all but 1, 2, or 3 of the physiological and morphological characteristics of NUN 09015 TOF (e.g. as listed in Table 1).

The morphological and/or physiological differences between plants according to the invention, i.e. NUN 09015 TOF or progeny thereof, or plants having all but 1, 2, or 3 of the physiological and morphological characteristics of NUN 09015 TOF (as listed in Table 1); and other known varieties can easily be established by growing NUN 09015 TOF next to the other varieties (in the same field, under the same environmental conditions), preferably in several locations which are suitable for said tomato cultivation, and measuring morphological and/or physiological characteristics of a number of plants (e.g., to calculate an average value and to determine the variation range/uniformity within the variety). For example, trials can be carried out in Acampo Calif., USA (N 38 degrees 07'261"/W 121 degrees 18'807", USA, whereby, maturity, days from seeding to harvest, plant habit, plant attitude, leaf shape, leaf color, blistering, numbers of flowers per leaf axil, number of calyx lobes, number of petals, fruit group, immature fruit color, mature fruit color, pungency, flavor, fruit glossiness, fruit size, fruit shape, average number of fruits per plant, seed size, seed weight, anthocyanin level, disease resistance, insect resistance, can be measured and directly compared for species of *Solanum*.

The morphological and physiological characteristics (and distinguishing characteristics) of NUN 09015 TOF, are provided in the Examples, in Table 1. Encompassed herein are also plants derivable from NUN 09015 TOF (e.g. by selfings and/or crossing and/or backcrossing with NUN 09015 TOF and/or progeny thereof) comprising all the physiological and morphological characteristics of NUN 09015 TOF listed in Table 1 as determined at the 5% significance level when grown under the same environmental conditions and/or comprising one or more (or all; or all except one, two or three) of the distinguishing characteristics as determined at the 5% significance level when grown under the same environmental conditions.

Also at-harvest and/or post-harvest characteristics of fruits can be compared, such as cold storage holding quality (browning), post-harvest rind firmness and/or flesh firmness, can be measured using known methods.

Flesh firmness can for example be measured using a penetrometer, e.g. by inserting a probe into the fruit flesh and determining the insertion force, or by other methods.

The morphological and/or physiological characteristics may vary somewhat with variation in the environment (such as temperature, light intensity, day length, humidity, soil, fertilizer use), which is why a comparison under the same environmental conditions is preferred. Colors can best be measured against The Munsell Book of Color (Munsell Color Macbeth Division of Kollmorgan Instruments Corporation) or using the Royal Horticultural Society Chart (World wide web at rhs.org.uk/Plants/RHS-Publications/RHS-colour-charts).

In a preferred embodiment, the invention provides for tomato fruits of variety NUN 09015 TOF, or a part of the fruit. In another embodiment, the invention provides for a container comprising or consisting of a plurality of harvested tomato fruits of NUN 09015 TOF, or progeny thereof, or a derived variety.

In yet a further embodiment, the invention provides for a method of producing a new tomato plant. The method comprises crossing a plant of the invention NUN 09015 TOF, or a plant comprising all but 1, 2, or 3 of the morphological and physiological characteristics of NUN 09015 TOF (as listed in Table 1), or a progeny plant thereof, either as male or as female parent, with a second tomato plant (or a wild relative of tomato) one or more times, and/or selfing a tomato plant according to the invention i.e. NUN 09015 TOF, or a progeny plant thereof, one or more times, and selecting progeny from said crossing and/or selfing. The second tomato plant may for example be a line or variety of the species *Solanum Lycopersicon, S. chilense, S. habrochaites, S. penelli, S. peruvianum S. pimpinellifolium* or other *Solanum* species.

Progeny are either the generation (seeds) produced from the first cross (F1) or selfing (S1), or any further generation produced by crossing and/or selfing (F2, F3, etc.) and/or backcrossing (BC1, BC2, etc.) one or more selected plants of the F1 and/or S1 and/or BC1 generation (or plants of any further generation, e.g. the F2) with another tomato plant (and/or with a wild relative of tomato). Progeny may have all the physiological and morphological characteristics of tomato variety NUN 09015 TOF when grown under the same environmental conditions and/or progeny may have (be selected for having) one or more of the distinguishing characteristics of tomato of the invention. Using common breeding methods such as backcrossing or recurrent selection, one or more specific characteristics may be introduced into NUN 09015 TOF, to provide or a plant comprising all but 1, 2, or 3 or more of the morphological and physiological characteristics of NUN 09015 TOF (as listed in Table 1).

The invention provides for methods of producing plants which retain all the morphological and physiological characteristics of NUN 09015 TOF. The invention provides also for methods of producing a plant comprising all but 1, 2, or 3 or more of the morphological and physiological characteristics of NUN 09015 TOF (e.g. as listed in Table 1), but which are still genetically closely related to NUN 09015 TOF. The relatedness can, for example be determined by fingerprinting techniques (e.g., making use of isozyme markers and/or molecular markers such as SNP markers, AFLP markers, microsatellites, minisatellites, RAPD markers, RFLP markers and others). A plant is "closely related" to NUN 09015 TOF if its DNA fingerprint is at least 80%, 90%, 95% or 98% identical to the fingerprint of NUN 09015 TOF. In a preferred embodiment AFLP markers are used for DNA fingerprinting (Vos et al. 1995, Nucleic Acid Research 23: 4407-4414). A closely related plant may have a Jaccard's Similarity index of at least about 0.8, preferably at least about 0.9, 0.95, 0.98 or more (Ince et al., (2010) Biochem. Genet. 48:83-95). The invention also provides plants and varieties obtained by these methods. Plants may be produced by crossing and/or selfing, or alternatively, a plant may simply be identified and selected amongst NUN 09015 TOF plants, or progeny thereof, e.g. by identifying a variant within NUN 09015 TOF or progeny thereof (e.g. produced by selfing) which variant differs from NUN 09015 TOF in one, two or three of the morphological and/or physiological characteristics (e.g. in one, two or three distinguishing characteristics), e.g. those listed in Table 1 or others.

By crossing and/or selfing also (one or more) single traits may be introduced into the variety of the invention i.e. NUN 09015 TOF (e.g., using backcrossing breeding schemes), while retaining the remaining morphological and physiological characteristics of NUN 09015 TOF and/or while retaining one or more distinguishing characteristics. A single trait converted plant may thereby be produced. For example, disease resistance genes may be introduced, genes responsible for one or more quality traits, yield, etc. Both single genes (dominant or recessive) and one or more QTLs (quantitative trait loci) may be transferred into NUN 09015 TOF by breeding with NUN 09015 TOF.

Any pest or disease resistance genes may be introduced into a plant according to the invention, i.e. NUN 09015 TOF, progeny thereof or into a plant comprising all but 1, 2, or 3 or more of the morphological and physiological characteristics of NUN 09015 TOF (e.g. as listed in Table 1). Resistance to one or more of the following diseases is preferably introduced into plants of the invention: Cucumber Mosaic Virus, Curly Top Virus, Tomato Mottle Virus, Potato Y Virus, Blotchey Ripening, Tobacco Etch Virus, the various Tobacco Mosaic Virus races, Concentric cracking, Tomato spotted wilt, Tomato yellows, Gold Fleck, Bacterial canker, Bacterial soft rot, Bacterial speck, Bacterial wilt, Anthracnose (*Gloeosporium piperatum*), Fusarium wilt (*F. oxysporum* races), Alternaria, Bacterial Spot (*Xanthomonas vesicatoria*), Nematode (*Meloidogyne incognita acrita*), Late blight (*Phytophthora infestans* races), Leaf mold (*Cladosporium fulvum* races), Colorado potato beetle, Spider mites, Whitefly and *Verticillium* Wilt (*Verticillium dahliae*).

Other resistance genes, against pathogenic viruses, fungi, bacteria, nematodes, insects or other pests may also be introduced.

Thus, invention also provides a method for developing a tomato plant in a tomato breeding program, using a tomato plant of the invention, or its parts as a source of plant breeding material. Suitable plant breeding techniques are recurrent selection, backcrossing, pedigree breeding, mass selection, mutation breeding and/or genetic marker enhanced selection. For example, in one aspect, the method comprises crossing NUN 09015 TOF or progeny thereof, or a plant comprising all but 1, 2, or 3 or more of the morphological and physiological characteristics of NUN 09015 TOF (e.g. as listed in Table 1), with a different tomato plant, and wherein one or more offspring of the crossing are subject to one or more plant breeding techniques selected from the group consisting of recurrent selection, backcrossing, pedigree breeding, mass selection, mutation breeding and genetic marker enhanced selection (see e.g. Vidaysky and Czosnek, (1998) Phytopathology 88(9): 910-4). For breeding methods in general see Principles of Plant Genetics and Breeding, 2007, George Acquaah, Blackwell Publishing, ISBN-13: 978-1-4051-3646-4.

The invention thus also provides a method of introducing a single locus conversion, or single trait conversion or introducing a desired trait, into a tomato plant according to the invention and/or into NUN 09015 TOF comprising:
(a) crossing a tomato plant of variety NUN 09015 TOF, a representative sample of seed of said variety having been deposited under Accession Number NCIMB 42622, with a second tomato plant comprising a desired single locus to produce F1 progeny plants;
(b) selecting F1 progeny plants that have the single locus to produce selected F1 progeny plants;
(c) crossing the selected progeny plants with a plant of NUN 09015 TOF, to produce backcross progeny plants;

(d) selecting backcross progeny plants that have the single locus and one or more (or all) distinguishing characteristics of tomato according to the invention and/or all the physiological and morphological characteristics of NUN 09015 TOF to produce selected backcross progeny plants; and (e) optionally repeating steps (c) and (d) one or more times in succession to produce selected second, third or fourth or higher backcross progeny plants that comprise the single locus and otherwise one or more (or all) the distinguishing characteristics of the tomatoes according to the invention and/or comprise all of the physiological and morphological characteristics of NUN 09015 TOF, when grown in the same environmental conditions. The invention further relates to plants obtained by this method.

The above method is provided, wherein the single locus conversion concerns a trait, wherein the trait is pest resistance or disease resistance.

In one embodiment the trait is disease resistance and the resistance is conferred to Cucumber Mosaic Virus, Curly Top Virus, Tomato Mottle Virus, Potato Y Virus, Blotchey Ripening, Tobacco Etch Virus, the various Tobacco Mosaic Virus races, Concentric cracking, Tomato spotted wilt, Tomato yellows, Gold Fleck, Bacterial canker, Bacterial soft rot, Bacterial speck, Bacterial wilt, Anthracnose (*Gloeosporium piperatum*), *Fusarium* wilt (*F. oxysporum* races), Alternaria, Bacterial Spot (*Xanthomonas vesicatoria*), Nematode (*Meloidogyne incognita acrita*), Late blight (*Phytophthora infestans* races), Leaf mold (*Cladosporium fulvum* races), Colorado potato beetle, Spider mites, Whitefly and *Verticillium* Wilt (*Verticillium dahliae*).

The invention also provides a tomato plant comprising at least a first set of the chromosomes of tomato variety NUN 09015 TOF, a sample of seed of said variety having been deposited under Accession Number NCIMB 42622; optionally further comprising a single locus conversion, wherein said plant has essentially all of the morphological and physiological characteristics of the plant comprising at least a first set of the chromosomes of tomato NUN 09015 TOF. In another embodiment, this single locus conversion confers a trait selected from the group consisting of male sterility, herbicide tolerance, insect resistance, pest resistance, disease resistance, environmental stress tolerance, modified carbohydrate metabolism and modified protein metabolism.

In one embodiment, NUN 09015 TOF may also be mutated (by e.g. irradiation, chemical mutagenesis, heat treatment, etc.) and mutated seeds or plants may be selected in order to change one or more characteristics of NUN 09015 TOF. Methods such as TILLING may be applied to tomato populations in order to identify mutants. Similarly, NUN 09015 TOF may be transformed and regenerated, whereby one or more chimeric genes are introduced into the variety or into a plant comprising all but 1, 2, 3, or more of the morphological and physiological characteristics (e.g. as listed in Table 1). Transformation can be carried out using standard methods, such as Agrobacterium tumefaciens mediated transformation or biolistics, followed by selection of the transformed cells and regeneration into plants. A desired trait (e.g. genes conferring pest or disease resistance, herbicide, fungicide or insecticide tolerance, etc.) can be introduced into NUN 09015 TOF, or progeny thereof, by transforming NUN 09015 TOF or progeny thereof with a transgene that confers the desired trait, wherein the transformed plant retains all the phenotypic and/or morphological and/or physiological characteristics of NUN 09015 TOF or the progeny thereof and contains the desired trait.

The invention also provides for progeny of tomato variety NUN 09015 TOF obtained by further breeding with NUN 09015 TOF. In one aspect progeny are F1 progeny obtained by crossing NUN 09015 TOF with another plant or S1 progeny obtained by selfing NUN 09015 TOF. Also encompassed are F2 progeny obtained by selfing the F1 plants. "Further breeding" encompasses traditional breeding (e.g., selfing, crossing, backcrossing), marker assisted breeding, and/or mutation breeding. In one embodiment, the progeny have one or more (or all) of the distinguishing characteristics mentioned further above when grown under the same environmental conditions. In a further embodiment the progeny have all the physiological and morphological characteristics of variety NUN 09015 TOF when grown under the same environmental conditions. In another embodiment the progeny have one, two, or three distinct traits (qualitative or quantitative) introduced into NUN 09015 TOF, while retaining all the other physiological and morphological characteristics of variety NUN 09015 TOF when grown under the same environmental conditions.

An EDV is a plant having one, two or three physiological and/or morphological characteristics which are different from those of NUN 09015 TOF and which otherwise has all the physiological and morphological characteristics of NUN 09015 TOF, wherein a representative sample of seed of variety NUN 09015 TOF has been deposited under Accession Number NCIMB 42622. In particular variants which differ from NUN 09015 TOF in none, one, two or three of the characteristics mentioned in Table 1 are encompassed.

In one aspect, the EDV differs from NUN 09015 TOF in one, two or three of the distinguishing morphological and/or physiological characteristics selected from 1) average length of mature fruit (along stem axis); 2 average diameter of mature fruit (at widest point); 3) average weight of mature fruit; 4) average number of locules; and 5) average number of flowers in inflorescence.

In another embodiment the EDV may differ from NUN 09015 TOF in one, two or three morphological or physiological characteristic other than the "distinguishing morphological and/or physiological characteristics" (or essential physiological and/or morphological characteristics) of NUN 09015 TOF selected from: 6) average number of nodes between early inflorescence; 7) typical fruit shape of type 7; 8) an average length of dedicel (from joint to calyx attachment); 9) pubescence on younger stems and 10) shape of blossom end.

Tomatos according to the invention, such as the variety NUN 09015 TOF, or its progeny, or a plant having all physiological and/or morphological characteristics but one, two or three which are different from those of NUN 09015 TOF, can also be reproduced using vegetative reproduction methods. Therefore, the invention provides for a method of producing plants, or a part thereof, of variety NUN 09015 TOF, comprising vegetative propagation of variety NUN 09015 TOF. Vegetative propagation comprises regenerating a whole plant from a plant part of variety NUN 09015 TOF (or from its progeny or from or a plant having all physiological and/or morphological characteristics but one, two or three, which are different from those of NUN 09015 TOF), such as a cutting, a cell culture or a tissue culture.

The invention also concerns methods of vegetatively propagating a plant of the invention. In certain embodiments, the method comprises the steps of: (a) collecting tissue or cells capable of being propagated from a plant of the invention; (b) cultivating said tissue or cells to obtain proliferated shoots; and (c) rooting said proliferated shoots, to obtain rooted plantlets. Steps (b) and (c) may also be reversed, i.e. first cultivating said tissue to obtain roots and then cultivating the tissue to obtain shoots, thereby obtaining rooted plantlets. The rooted plantlets may then be further grown, to obtain plants. In one embodiment, the method further comprises step (d) growing plants from said rooted plantlets The invention also provides for a vegetatively propagated plant of variety NUN 09015 TOF (or from its progeny or from or a plant having all but one, two or three physiological and/or morphological characteristics which are different from those of NUN 09015 TOF, or a part thereof, having one or more distinguishing characteristics and/or all the morphological and physiological characteristics of NUN 09015 TOF (except for the characteristics differing), when grown under the same environmental conditions.

Parts of NUN 09015 TOF (or of its progeny or of a plant having all physiological and/or morphological characteristics but one, two or three which are different from those of NUN 09015 TOF) encompass any cells, tissues, organs obtainable from the seedlings or plants, such as but not limited to: tomato fruits or parts thereof, cuttings, hypocotyl, cotyledon, pollen and the like. Such parts can be stored and/or processed further. Encompassed are therefore also food or feed products comprising one or more of such parts, such as canned, chopped, cooked, roasted, in a sauce, in a sandwich, pasted, puréed or concentrated, juiced, frozen, dried, pickled, or powdered tomato fruit from NUN 09015 TOF or from progeny thereof, or from a derived variety, such as a plant having all but one, two or three physiological and/or morphological characteristics which are different from those of NUN 09015 TOF.

In one aspect haploid plants and/or double haploid plants of NUN 09015 TOF, or a plant having all but one, two or three physiological and/or morphological characteristics which are different from those of NUN 09015 TOF, or progeny of any of these, are encompassed herein. Haploid and double haploid (DH) plants can, for example, be produced by cell or tissue culture and chromosome doubling agents and regeneration into a whole plant. For DH production chromosome doubling may be induced using known methods, such as colchicine treatment or the like.

Also provided are plant parts derived from variety NUN 09015 TOF (or from its progeny or from a plant having all but one, two or three physiological and/or morphological characteristics which are different from those of NUN 09015 TOF D), or from a vegetatively propagated plant of NUN 09015 TOF (or from its progeny or from a plant having all but one, two or three physiological and/or morphological characteristics which are different from those of NUN 09015 TOF), being selected from the group consisting of: harvested fruits or parts thereof, pollen, cells, leaves or parts thereof, petioles, cotyledons, hypocotyls, shoots or parts thereof, stems or parts thereof, roots or parts thereof, cuttings, or flowers.

In one embodiment, the invention provides for extracts of a plant described herein and compositions comprising or consisting of such extracts. In a preferred embodiment, the extract consists of or comprises tissue of a plant described herein or is obtained from such tissue.

In still yet another aspect, the invention provides a method of determining the genotype of a plant of the invention comprising detecting in the genome (e.g., a sample of nucleic acids) of the plant at least a first polymorphism. The method may, in certain embodiments, comprise detecting a plurality of polymorphisms in the genome of the plant, for example by obtaining a sample of nucleic acid from a plant and detecting in said nucleic acids a plurality of polymorphisms. The method may further comprise storing the results of the step of detecting the plurality of polymorphisms on a computer readable medium The invention also provides for a food or feed product comprising or consisting of a plant part described herein wherein the plant part can be identified as a part of the plant of the invention. Preferably, the plant part is a tomato fruit or part thereof and/or an extract from a fruit or another plant part described herein. The food or feed product may be fresh or processed, e.g., dried, grinded, powdered, pickled, chopped, cooked, roasted, in a sauce, in a sandwich, pasted, puréed or concentrated, juiced, pickled, canned, steamed, boiled, fried, blanched and/or frozen, etc.

For example, containers such as cans, boxes, crates, bags, cartons, Modified Atmosphere Packagings, films (e.g. biodegradable films), etc. comprising plant parts of plants (fresh and/or processed) described herein are also provided herein.

Marketable tomato fruits are generally sorted by size and quality after harvest. Alternatively the tomato fruits can be sorted by expected shelf life. pH of Brix.

Tomatos may also be grown for use in grafting or inosculation as rootstocks (stocks) or scions (cions). Typically, different types of tomatoes are grafted to enhance disease resistance, which is usually conferred by the rootstock, while retaining the horticultural qualities usually conferred by the scion. It is not uncommon for grafting to occur between cultivated tomato varieties and related *Solanum* species. Methods of grafting and vegetative propagation are well-known in the art.

So in one aspect the invention relates to a plant comprising a rootstock or scion of NUN 09015 TOF.

Using methods known in the art like "reverse breeding", it is possible to produce parental lines for a hybrid plant such as NUN 09015 TOF; where normally the hybrid is produced from the parental lines. Such methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from WO2014076249 or from Nature Protocols Volume: 9, Pages: 761-772 (2014) DOI: doi:10.1038/nprot.2014.049, which are enclosed by reference. Such method for producing parental lines for a hybrid organism, comprises the steps of: a) defining a set of genetic markers that are present in a heterozygous form (H) in a partially heterozygous starting organism; b) producing doubled haploid lines from spores of the starting organism: c) genetically characterizing the doubled haploid lines thus obtained for the said set of genetic markers to determine whether they are present in a first homozygous form (A) or in a second homozygous form (B); d) selecting at least one pair of doubled haploid lines that have complementary alleles for at least a subset of the genetic markers, wherein each member of the pair is suitable as a parental line for a hybrid organism.

Thus in one aspect, the invention relates to a method of producing a combination of parental lines of a plant of the invention (NUN 09015 TOF) comprising the step of making double haploid cells from haploid cells from the plant of the invention (NUN 09015 TOF) or a seed of that plant; and optionally crossing these parental lines to produce and collect seeds. In another aspect, the invention relates to a combination of parental lines produced by this method. In still another aspect said combination of parental lines can be used to produce a seed or plant of NUN 09015 TOF when these parental lines are crossed. In still another aspect, the invention relates to a combination of parental lines from which a seed or plant having all but one, two or three physiological and/or morphological characteristics which are different from those of NUN 09015 TOF can be produced or in another aspect, wherein a seed or plant having the distinguishing characteristics 1)-5) or 1)-10) of NUN 09015 TOF, as herein defined, can be produced when grown under the same environmental conditions. In still another aspect, the invention relates to a combination of parental lines from which a seed or plant having all the characteristics of NUN 09015 TOF as defined in Table 1 can be produced when grown under the same conditions.

All documents (e.g., patent publications) are herein incorporated by reference in their entirety. Cited references:

In one embodiment of the invention, the first step in "crossing" comprises planting seeds of a first and a second parent tomato plant, often in proximity so that pollination will occur for example, mediated by insect vectors. Alternatively, pollen can be transferred manually. Where the plant is self-pollinated, pollination may occur without the need for direct human intervention other than plant cultivation.

Development of NUN 09015 TOF

The hybrid NUN 09015 TOF was developed from a male and female proprietary inbred line of Nunhems. The female and male parents were crossed to produce hybrid (F1) seeds of NUN 09015 TOF The seeds of NUN 09015 TOF can be grown to produce hybrid plants and parts thereof (e.g. tomato). The hybrid NUN 09015 TOF can be propagated by seeds or vegetative.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant concluded that NUN 09015 TOF is uniform and stable.

DANIELA is considered to be the most similar variety to NUN 09015 TOF. DANIELA is a commercial variety from Sakata. In Table 1 a comparison between NUN 09015 TOF and DANIELA is shown based on a greenhouse trial in the USA. Trial location I: Acampo, Calif., USA (coordinates: 38°192873"N 121°232637"W). Seeding date: Apr. 3, 2014. Transplanting date: May 12, 2014. Harvest date: July, 2014.

Two replications of 50 plants each, from which 15 plants or plant parts were randomly selected, were used to measure characteristics. In Table 1 the USDA descriptors of NUN 09015 TOF (this application) and reference DANIELA (commercial variety) are listed.

In accordance with one aspect of the present invention, there is provided a plant having the physiological and morphological characteristics of tomato variety NUN 09015 TOF. A description of the physiological and morphological characteristics of tomato variety NUN 09015 TOF is presented in Table 1.

TABLE 1

Objective description of varieties NUN 09015 TOF and DANIELA

|  | NUN 09015 TOF | DANIELA |
|---|---|---|
| 1. Seedling | | |
| Anthocyanin in hypocotyl | 2 | 2 |
| 1 = absent, 2 = present | | |
| habit of 3-4 week old seedling | 1 | 1 |
| 1 = normal, 2 = compact | | |

TABLE 1-continued

Objective description of varieties NUN 09015 TOF and DANIELA

|  | NUN 09015 TOF | DANIELA |
|---|---|---|
| 2. Mature plant | | |
| Height | NA | NA |
| Growth type | 1 | 1 |
| 1 = indeterminate; 2 = determinate | | |
| Form | 2 | 2 |
| 1 = lax; 2 = normal; 3 = compact; 4 = dwarf; 5 = brachytic | | |
| Size of canopy (compared to similar form) | 2 | 2 |
| 1 = small; 2 = medium; 3 = large | | |
| Habit | 1 | 1 |
| 1 = sprawling; 2 = semi-erect; 3 = erect (Dwarf Champion) | | |
| 3. Stem | | |
| Branching | 2 | 2 |
| 1 = sparse (Brehm's Solid Red; Fireball); 2 = intermediate (Westover); 3 = profuse (UC 82) | | |
| Branching at cotyledon or first leafy node | 2 | 2 |
| 1 = present; 2 = absent | | |
| Number of nodes before first inflorescence | 3 | 3 |
| Number of nodes between early ($1^{st}$ to $2^{nd}$, $2^{nd}$ to $3^{rd}$) inflorescence | 2 | 2 |
| Number of nodes between later developing inflorescences | NA | NA |
| Pubescence on younger stems | 3 | 2 |
| 1 = smooth (no long hairs); 2 = sparsely hairy (scattered long hairs); 3 = moderately hairy; 4 = densely hairy or wooly | | |
| 4. Leaf | | |
| Type: | 1 | 1 |
| 1 = tomato; 2 = potato (Trip-L-Crop) | | |
| Morphology (corresponding to Exhibit C illustration) | 2 | 2 |
| Margins of major leaflets | 2 | 2 |
| 1 = absent; 2 = shallowly toothed or scalloped; 3 = deeply toothed or cut, sps. towards base | | |
| Marginal rolling or wiltiness | 1 | 1 |
| 1 = absent; 2 = slight; 3 = moderate; 4 = strong | | |
| Onset of leaflet rolling | NA | NA |
| 1 = early-season; 2 = mid-season; 3 = late-season | | |
| Surface of major leaflets | 2 | 2 |
| 1 = smooth; 2 = rogues (bumpy or veiny) | | |
| Pubescence | 2 | 2 |
| 1 = smooth (no long hairs); 2 = normal; 3 = hirsute; 4 = wooly | | |
| 5. Inflorescence | | |
| Type | 1 | 1 |
| 1 = simple, 2 = forked, 3 = compound | | |
| Number of flowers in inflorescence | 7.7 | 5.87 |
| Leafy or "running" inflorescences | 1 | 2 |
| 1 = absent, 2 = occasional, 3 = frequent | | |
| 6. Flower | | |
| Calyx | 1 | 1 |
| 1 = normal, lobes awl-shaped; 2 = macrocalyx, lobes large, leaflike; 3 = fleshy | | |
| Calyx-lobes | NA | 1 |
| 1 = shorter the corolla; 2 = approx., equaling corolla; 3 = distinctly longer than corolla | | |
| Corolla color | 1 | 1 |
| 1 = yellow: 2 = old gold; 3 = white or tan | | |
| Style pubescence | 2 | 2 |
| 1 = absent; 2 = sparse; 3 = dense | | |
| Anthers | 1 | 1 |
| 1 = all fused into tube; 2 = separating into 2 or more groups at anthesis | | |

TABLE 1-continued

Objective description of varieties NUN 09015 TOF and DANIELA

| | NUN 09015 TOF | DANIELA |
|---|---|---|
| Fasciation (1st flower of 2$^{nd}$ or 3$^{rd}$ inflorescence)<br>1 = absent; 2 = occasionally present;<br>3 = frequently present<br>7. fruit | 1 | 1 |
| Typical shape (corresponding to Exhibit C illustration of USDA Objective Description of Variety Tomato) | 7 | 2 |
| Shape of transverse section<br>1 = round; 2 = flattened; 3 = angular; 4 = irregular | 1 | 1 |
| Shape of stem end<br>1 = flat; 2 = indented | 1 | 1 |
| Shape of blossom end<br>1 = indented; 2 = flat; 3 = nippled; 4 = tapered | 3 | 3 |
| Shape of pistil scar<br>1 = dot; 2 = stellate; 3 = linear; 4 = irregular | 1 | 1 |
| Abscission layer<br>1 = present (pedicellate);<br>2 = absent (jointless) | 1 | 1 |
| Point of detachment of fruit at harvest<br>1 = at pedicel joint; 2 = at calyx attachment | 1 | 1 |
| Length of dedicel (from joint to calyx attachment) | 15.6 mm | 13.1 |
| Length of mature fruit (stem axis) | 62 mm | 48.9 |
| Diameter of fruit at widest point | 47 mm | 57.8 |
| Weight of mature fruit | 71.3 g | 92.47 |
| Number of locules<br>1 = two; 2 = three or four; 3 = five or more | 1 | 2 |
| Fruit surface<br>1 = smooth; 2 = slightly rough;<br>3 = moderately rough or ribbed | 1 | 1 |
| Fruit base color (mature-green stage)<br>1 = light green (Lanal; VF 145-F5);<br>2 = light gray-green; 3 = apple or medium green (Heinz 1439 VF);<br>4 = yellow green; 5 = dark green | 3 | 3 |
| Fruit pattern (mature-green stage)<br>1 = uniform green; 2 = green-shouldered;<br>3 = radial stripes on sides of fruit | 1 | 2, |
| Shoulder color if different from base<br>1 = dark green; 2 = grey green;<br>3 = yellow green | NA | 1 |
| Fruit color full ripe:<br>1 = white; 2 = yellow; 3 = orange; 4 = pink;<br>5 = red; 6 = brownish 7 = greenish; 8 = other | 5 | 5 |
| Flesh color full ripe:<br>1 = yellow; 2 = pink; 3 = red/crimson;<br>4 = orange; 5 other | 3 | 3 |
| Flesh color:<br>1 = uniform; 2 = with lighter and darker areas in walls | 1 | 1 |
| Locular gel color of table-ripe fruit<br>1 = green; 2 = yellow; 3 = red | 3 | 3 |
| Ripening<br>1 = blossom to stem end; 2 = uniform | 2 | 2 |
| Ripening<br>1 = inside out; 2 = uniformity; 3 = outside in | 2 | 2 |
| Stem scar size:<br>1 = small (Roma); 2 = medium (Rutgers); 3 = large | 1 | 1 |
| Core:<br>1 = coreless (absent or smaller than 6 × 6 mm); 2 = present | 1 | 1 |
| Epidermis color:<br>1 = colorless; 2 = yellow | 2 | 2 |
| Epidermis:<br>1 = normal; 2 = easy-peel | 1 | 1 |
| Epidermis texture:<br>1 = tender; 2 = average; 3 = tough | 2 | 2 |
| Thickness of pericarp: | 7.7 mm | 7.3 mm |
| 9. Disease and Pest Reaction<br>1 highly resistant, 2 intermediate resistance,<br>3 susceptible, 4 not determined | NA | NA |
| 10. Chemistry and composition of full-ripe fruits | NA | NA |
| 11. Phenology<br>12. Adaptation | NA | NA |
| Culture<br>1 = field, 2 = greenhouse | 2 | 2, 1 |
| Principle use<br>5 = other (specify) | 2 | 2 |
| Regions to which adaptation has been demonstrated:<br>1 = Northeast; 2 = Mid Atlantic;<br>3 = Southeast; 4 Florida;<br>5 = Great Plains, 6 = south central;<br>7 = Intermountain West; 8 = Northwest;<br>9 = California (Sacramento and Upper San Joaquin Valley);<br>10 = California (Coastal Areas); 11 California (Southern San Joaquin Valley & desserts) | 9 | 9 |

Table 1 contains typical values. Values may vary due to environment. Other values that are substantially equivalent are also within the scope of the invention. N.A.=not applicable; n.r.=not recorded.

DEPOSIT INFORMATION

A total of 2500 seeds of the hybrid variety NUN 09015 TOF were deposited according to the Budapest Treaty by Nunhems B.V. on Aug. 9, 2016, at the NCIMB Ltd., Ferguson Building, Craibstone Estate, Bucksburn, Aberdeen AB21 9YA, United Kingdom (NCIMB). The deposit has been assigned or NCIMB 42622 A deposit of NUN NUN 09015 TOF and of the male and female parent line is also maintained at Nunhems B.V. Access to the deposit will be available during the pendency of this application to persons determined by the Director of the U.S. Patent Office to be entitled thereto upon request. Subject to 37 C.F.R. §1.808 (b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

What is claimed is:

1. A plant, plant part or seed of tomato variety NUN 09015 TOF, wherein a representative sample of said seed has been deposited under Accession Number NCIMB 42622.

2. A plant or part thereof grown from the seed of claim 1.

3. The plant part of claim 2, further defined as a leaf, pollen, an ovule, a fruit, a scion, a rootstock, cutting, flower or a cell.

4. A *Solanum* plant, or a part thereof, wherein said plant, or part thereof has all the morphological and physiological characteristics of tomato variety NUN 09015 TOF as listed in Table 1, and wherein a representative sample of seed of said variety has been deposited under Accession Number 42622.

5. A tissue or cell culture of regenerable cells of the plant of claim 2.

6. A tomato plant regenerated from the tissue or cell culture of claim 5, wherein the plant has all of the physiological and morphological characteristics of the plant of tomato variety NUN 09015 TOF as listed in Table 1 when determined at the 5% significance level, and wherein a representative sample of seed of NUN 09015 TOF has been deposited under Accession Number 42622.

7. A tomato plant regenerated from the tissue or cell culture of claim 5, wherein the plant has all of the physiological and morphological characteristics of the plant of tomato variety NUN 09015 TOF when determined at the 5% significance level, and wherein a representative sample of seed of NUN 09015 TOF has been deposited under Accession Number 42622.

8. A method of producing a plant comprising vegetative propagating the plant, or a part thereof, of claim 2.

9. The method of claim 8, further comprising regenerating a whole plant from a part of the plant of tomato variety NUN 09015 TOF, wherein a representative sample of seed of tomato variety NUN 09015 TOF has been deposited under Accession Number 42622.

10. The method of claim 8, wherein said part is a cutting, a cell culture or a tissue culture.

11. A plant produced by the method of claim 8, wherein the plant has all the morphological and physiological characteristics of a plant of tomato variety NUN 09015 TOF when determined at the 5% significance level, and wherein a representative sample of seed of said variety has been deposited under Accession Number NCIMB 42622.

12. A method of producing a tomato plant, comprising crossing the plant of claim 2 with a second tomato plant one or more times, selecting progeny from said crossing, and optionally allowing the progeny to form seed.

13. A method of producing a tomato plant, comprising selfing the plant of claim 2 one or more times, selecting progeny from said selfing, and optionally allowing the progeny to form seed.

14. A method of introducing a desired trait into a tomato plant comprising:
  a) crossing the plant of claim 2 with a second tomato plant that comprises a desired trait to produce F1 progeny;
  b) selecting an F1 progeny that comprises a desired trait;
  c) optionally selfing the F1 progeny one or more times to produce F2, F3, or further generation selfing progeny,
  d) crossing the selected F1 progeny or the selfing progeny with the plant of claim 2 to produce backcross progeny;
  e) selecting backcross progeny comprising the desired trait and which otherwise has all the physiological and morphological characteristic of the plant of claim 2; and optionally
  f) repeating steps (d) and (e) one or more times in succession to produce selected higher backcross progeny that comprises the desired trait.

15. A plant comprising the scion or rootstock of claim 3.

* * * * *